United States Patent [19]

Bowman et al.

[11] 4,087,471

[45] May 2, 1978

[54] FIXED BED PROCESS FOR THE PRODUCTION OF T-BUTANOL

[75] Inventors: William G. Bowman; William P. Stadig, both of Houston, Tex.

[73] Assignee: Petro-Tex Chemical Corporation, Houston, Tex.

[21] Appl. No.: 799,103

[22] Filed: May 20, 1977

[51] Int. Cl.$^2$ ............................................. C07C 29/04
[52] U.S. Cl. ........................................ 568/899; 44/56; 260/683 R
[58] Field of Search .......................................... 260/641

[56] References Cited

U.S. PATENT DOCUMENTS

| | | | |
|---|---|---|---|
| 2,477,380 | 7/1949 | Kreps et al. | 260/641 |
| 2,574,325 | 11/1951 | Gislon | 260/639 R |
| 2,678,332 | 5/1954 | Cottle | 260/475 |
| 2,813,908 | 11/1957 | Young | 260/641 |
| 3,257,469 | 6/1966 | Kovach | 260/641 |
| 3,285,977 | 11/1966 | Henke et al. | 260/641 |
| 3,328,471 | 6/1967 | Kronig et al. | 260/641 |
| 3,548,013 | 12/1970 | Rosscup et al. | 260/641 |
| 3,950,442 | 4/1976 | Vogel et al. | 260/641 |
| 3,989,762 | 11/1976 | Ester | 260/641 |
| 3,994,983 | 11/1976 | Webers et al. | 260/641 |

Primary Examiner—Joseph E. Evans
Attorney, Agent, or Firm—Kenneth H. Johnson

[57] ABSTRACT

An improved process for the preparation of tertiary butyl alcohol comprising passing isobutene and water in a molar ratio of water to isobutene in the range of 0.06 to 0.24 : 1 or preferably less than 0.2 : 1 through a fixed bed acidic cation exchange resin, producing only a hydrocarbon phase, removing the hydrocarbon phase, splitting the hydrocarbon phase, and recycling a portion thereof to the reaction. The recycle provides the means to control the temperature of the reaction by cooling the recycle, and suppresses or inhibits the production of isobutene polymers.

18 Claims, 1 Drawing Figure

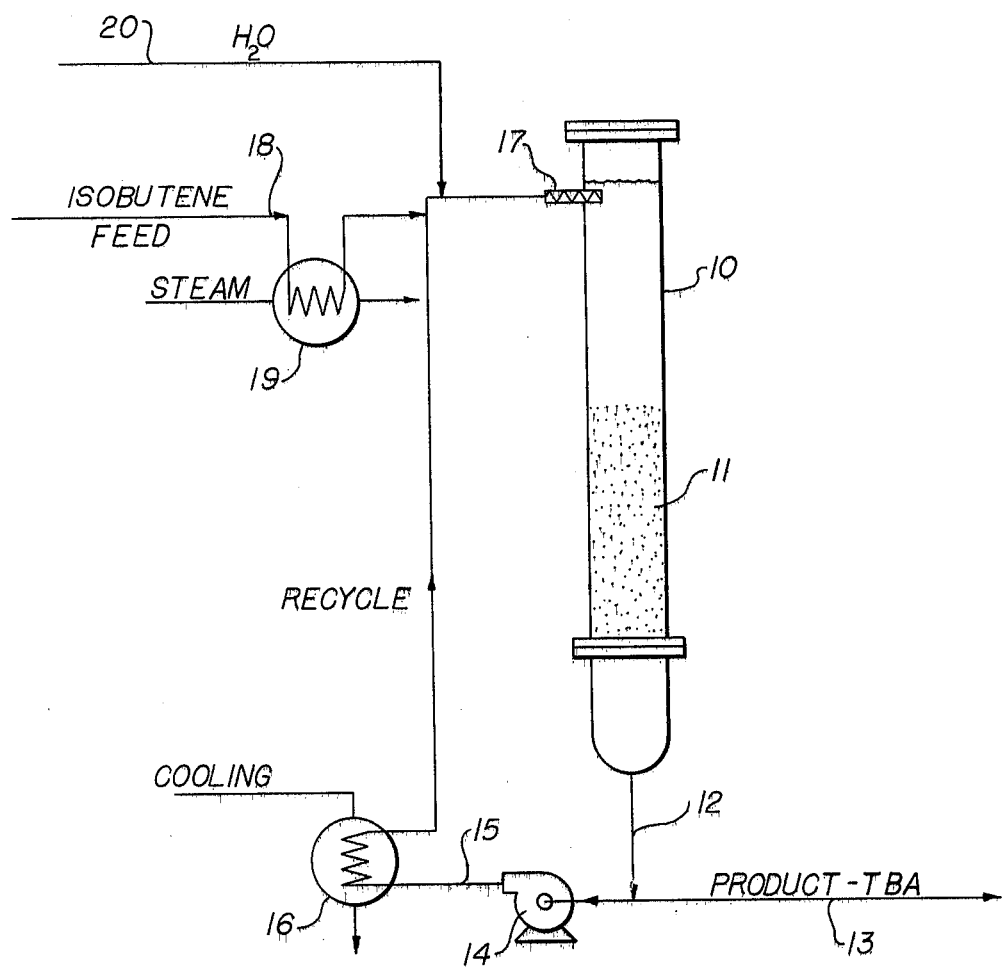

4,087,471

FIXED BED PROCESS FOR THE PRODUCTION OF T-BUTANOL

BACKGROUND OF THE INVENTION

This invention relates to a process for the production of tertiary butanol from isobutene. More particularly, the invention relates to a fixed bed catalytic process.

The acid catalysis of the reaction of isobutene and water to produce t-butanol is well known. More recently, acid ion exchange resins have been used as the catalysts, e.g., British Patent Specifications 1,390,164 and 1,396,488, where the reaction of propylene and water was illustrated in a fixed bed acidic ion exchange resin.

Commercial operations would have to be continuous to be feasible. Fixed bed procedures were initially proposed as the most desirable because of simplicity of operation, i.e., water and isobutene are passed over the catalyst, the phases separated and t-butanol separated from the organic phase and/or the water phase. The reaction is exothermic and temperature control has presented a problem. Temperature control may be effected by increasing the amount of water in the reaction. However, another problem which is a serious detriment is a rapid increase in by-product formation. At the beginning of the process, the reaction proceeds as expected, with high selectivity for the production of t-butanol. Side reactions begin and increase as the reaction proceeds, with a substantial reduction of t-butanol formation. The side reactions include particularly polymerization, which is uncontrolled and from which results diisobutene, triisobutene, higher oligomers, and codimers of isobutene and n-butenes.

The formation of diisobutene and triisobutene may not be particularly undesirable since these materials are of commercial interest. The higher oligomers, however, are substantially waste and in some cases, are dark, gummy materials, which can foul equipment or otherwise interfere with the process. Furthermore, the uncontrolled side reaction is a detriment, since product distribution cannot be adjusted as desired. It should also be noted in the prior art that by-product selectivity could be reversed only by the cessation of the reaction, back-washing of the catalyst with water or replacement of the catalyst.

U.S. Pat. No. 3,328,471, issued to Krönig et al, appreciated these problems in the fixed bed system, and determined that the problems as described in the fixed bed were not soluble and abandoned the fixed bed for a fluidized system. The Krönig et al process consists of isobutene, water and finely granular cation exchange resin, which are vigorously mixed in a reactor(s), separated into hydrocarbon phase and a water phase, which contains the resin catalyst. t-Butanol is recovered by distillation from the hydrocarbon phase, and the water-resin phase is recycled to the reactor. Catalyst and water, which are lost, are made up in order to maintain the desired ratios. This system is cooled at a number of points, thus making temperature control easy. The selectivity to t-butanol remained high. Because the Krönig et al system depends on emulsification of the three-component system to obtain reaction, the use of an emulsifier is suggested.

The fluidized system of Krönig et al is inherently less desirable because the catalyst is mixed into the reactants and some portion may remain in the hydrocarbon fraction, requiring an additional separation, whereas the fixed bed does not, i.e., the catalyst will generally remain in the aqueous phase. However, the agitation of the fluidized system results in disintegration of some catalysts and the fines are likely to be dispersed in both the aqueous and hydrocarbon phases.

The disintegration of the catalysts in the fluidized bed requires frequent makeup to maintain the reaction because the amount of catalyst present in this type of system is generally less than in a fixed bed. Larger amounts of aqueous phase and catalyst may, of course, be employed in the fluidized bed; however, handling problems and energy required to pump excess catalyst through the system are contraindicative of that. It should also be appreciated that larger amounts of catalyst will be lost when larger amounts of the catalyst are employed, although makeup for maintaining the reaction may be less frequent.

The energy requirements of the fluidized system are also greater for any given amount of reactants than the fixed bed, since the pumping of the aqueous slurry and the agitation of the reactants are excessive beyond fixed bed handling.

As noted above, the fluidized system may be improved by the use of emulsifiers. The emulsifiers are contaminants which may require special handling for their removal.

It is an advantage of the present invention that benefits of the fixed bed isobutene hydrations and the fluidized system are both obtained. It is another advantage of the present invention that an improved fixed bed isobutene hydration process for the preparation of t-butanol has been obtained. It is a particular feature of the present invention that a method of suppressing (or controlling) isobutene polymerization in a fixed catalyst bed has been obtained. It is also a feature of the present invention that temperature control of the fixed bed hydration has been obtained. These and other advantages and features will be more apparent from the further discussion of the invention. Another advantage is the elimination of the water phase from the product stream and the resultant corrosion problems therefrom.

DRAWINGS

The FIGURE is a schematic representation of the hydration process of the present invention.

SUMMARY OF THE INVENTION

Briefly stated, the present invention is a process for the preparation of t-butanol (TBA) comprising passing water and isobutene in a mol ratio of water : isobutene in the range of 0.06 to 0.24, preferably less than 0.24 mol of water per mol of isobutene, e.g., 0.2 or less mol of water through a fixed bed of acidic cation ion exchange resin in liquid phase, at a temperature in the range of 65° to 150° C, preferably no higher than 120° C, for a sufficient time to react the water and isobutene, producing only a hydrocarbon phase product, recovering said hydrocarbon phase, containing t-butanol, splitting said hydrocarbon phase, cooling a portion thereof to a temperature in the range of 15° to 110° C, and recycling the cooled hydrocarbon phase to the reaction. Tertiary butanol may be recovered from a portion of the product which is not recycled.

Generally, the isobutylene is fed as a liquid mixture of $C_4$ hydrocarbons, containing principally, saturated and monoolefinic compounds, and is fed to a fixed bed reactor containing a cation exchange resin in the hydrogen or acid form, such as Amberlyst 15. The amount of water injected in or mixed with the feed is controlled or adjusted, in accordance with the invention, such that the catalyst (resin) is maintained in a partially dehydrated condition, and there is no free water phase leaving the reactor, or the catalyst bed.

DETAILED DESCRIPTION OF THE INVENTION AND PREFERRED EMBODIMENTS

A preferred process for the preparation of t-butanol comprising:

a. feeding a stream containing isobutene;
b. intimately mixing water and said stream in a mol ratio of 0.06 to 0.24 : 1, water; isobutene;
c. contacting said mixture of water and isobutene with a granular fixed bed acidic cation exchange resin for a sufficient time to react water and isobutene at a temperature of reaction in the fixed bed in the range of 65° to 150° C;
d. producing only a hydrocarbon phase product stream containing t-butanol;
e. splitting the product passing from said fixed bed into two portions;
f. recovering and removing one portion of said hydrocarbon phase product;
g. cooling one portion said hydrocarbon phase product to a temperature in the range of 15° to 110° C; and
h. recycling said cooled hydrocarbon phase product portion to step (a) or (b).

The hydrocarbon phase portion which is recycled is preferably recycled continuously to step (a). t-Butanol is preferably recovered from the product of step (f).

The cooled hydrocarbon phase product which is recycled to the reaction provides the temperature control of the reaction. By adjusting the temperature of this portion, the catalyst bed temperature is maintained in the desired range. The volume ratio of recycle of hydrocarbon product : fresh isobutene feed may vary, generally in the range of from more than 0, e.g., 0.1, to 50 : 1, more preferably about 5 to 30 : 1 or up to about 20 : 1. Substantially, the only water added to the system is that water for use in the reaction. The amount of tertiary butanol in the product can vary widely, depending on the ratio of water to isobutene, as can be appreciated, but generally, will be present in a mol ratio of TBA : isobutene (unreacted) in the range of 0.1 to 5 : 1. Since the reaction is an equilibrium reaction, the presence of t-butanol in the recycle does reduce the percent conversion a small amount, but this small conversion loss is more than offset by the reduction in by-product polymer and the elimination of the water phase handling.

In U.S. Pat. No. 3,328,471, Krönig et al determined that the fixed bed system was the reason for the decline in t-butanol selectivity and urge that only the stirred, fluidized system could overcome that problem and the temperature control. The present inventors have surprisingly found otherwise, and have solved the problems noted by Krönig et al, simply by recycle of a portion of the hydrocarbon phase product with appropriate cooling; hence, the simpler, less expensively operated fixed bed system is now suitable for continuous commercial application.

The present process is preferably carried out in a substantially vertical fixed catalyst bed; for example, a bed of cation exchange resin supported in a vertical reactor. Such reactors may range from a few inches to several feet in diameter. The depth of the bed may vary within a wide range with the reactant-catalyst contact time being adjusted by the flow of the reactants therethrough. Generally, LHSV of the isobutene 0.1 to 3.0 are employed with LHSV of 0.5 to 2.0 being preferred as based on fresh feed (i.e., excluding recycle).

The flow in the reactor may be upward or downward, with the downflow being preferred. Similarly, counterflow may be employed for the recycle and hydrocarbon; however, concurrent flow is preferred. It is believed that better reactant-catalyst contact occurs in the concurrent downward flow. The hydrocarbon appears to be the continuous phase. Contact between the catalyst, hydrocarbon and water, which is heavier than the hydrocarbon, is better in downward flow.

The reaction is conducted at 65° to 150° C in the reactor. There may be a temperature gradient through the bed, which preferably, is no greater than 10° to 25° C. A preferred temperature range for the reaction is 90° to 120° C. The reaction is carried out under sufficient pressure to maintain a liquid phase system, e.g., 16 to 25 atmospheres. The temperature of hydrocarbon feed and the water feed to the reactor is adjusted to maintain the temperature in the catalyst bed as specified, which will generally mean heating the hydrocarbon feed and cooling (at least after startup) the hydrocarbon recycle. These adjustments are made for each reactor, ratio of reactant and the like, and are easily within the skill of the mechanic in the art. The heating and cooling mentioned above may be carried on simultaneously by mixing the two streams.

The liquid hydrocarbon and water feed may be fed through a single line or separate lines into the reactor. Trickle or spray techniques may be used to introduce the reactants into the reactor.

The hydrocarbon phase product which is not recycled may be fractionated to recover t-butanol and unreacted isobutene, which may recycled. Tertiary butanol may be used as an octane improver for gasolines in amounts up to 20 percent. Since it is a tertiary alcohol, it is not subject to autoxidation on standing, for example, in storage, and remains stable in the gasoline without special consideration.

The isobutene reactant may comprise up to 100 percent of the hydrocarbon feed to the reactor, generally 5 to 100 percent. Frequently, the isobutene is contained in a feed stream which is substantially comprised of $C_4$ hydrocarbons, such as butene-1, butene-2 and butane. Butadiene is reactive in the process of this invention and may be desirably removed prior thereto, although amounts of 0.5 percent or less, do not present so much of a problem as to require removal.

The water is present in the reactor in an amount far less than the stoichiometric amount, generally, 0.06 to less than 0.24 mol of water per mol of isobutene. The water is substantially free of cations. Distilled or demineralized (deionized) water may be employed. The water and isobutene may be intimately mixed by known methods to form an emulsion which is passed through the catalyst bed.

Molar ratios of water to isobutene less than 0.6 : 1, i.e., 0.001 to less than 0.06 : 1, result in substantial amounts of dimer being formed, and a companion application entitled "DIMERIZATION OF ISOBUTENE", S.N. 810,644 filed 6-27-1977, directed to that process, has been filed concurrently herewith by the inventors. These processes are closely related and may be run in the same reactor with the same reactants by adjustment of the molar ratio of water to isobutene.

The cation resins are those which have been used in the prior art for this reaction. Catalysts suitable for the new process are cation exchangers, which contain sulfonic acid groups, and which have been obtained by polymerization or copolymerization of aromatic vinyl compounds followed by sulfonation. Examples of aromatic vinyl compounds suitable for preparing polymers or copolymers are: styrene, vinyl toluene, vinyl naphthalene, vinyl ethylbenzene, methyl styrene, vinyl chlorobenzene and vinyl xylene. A large variety of methods may be used for preparing these polymers; for example, polymerization alone or in admixture with other monovinyl compounds, or by crosslinking with polyvinyl compounds; for example, with divinyl benzenes, divinyl toluenes, divinylphenylethers and others. The polymers may be prepared in the presence or absence of solvents or dispersing agents, and various polymerization initiators may be used, e.g., inorganic or organic peroxides, persulfates, etc.

The sulfonic acid group may be introduced into these vinyl aromatic polymers by various known methods; for example, by sulfating the polymers with concentrated sulfuric acid or chlorosulfonic acid, or by copolymerizing aromatic compounds which contain sulfonic acid groups (see e.g., U.S. Pat. No. 2,366,007). Further sulfonic acid groups may be introduced into these polymers which already contain sulfonic acid groups; for example, by treatment with fuming sulfuric acid, i.e., sulfuric acid which contains sulfur trioxide. The treatment with fuming sulfuric acid is preferably carried out at 0° to 150° C, and the sulfuric acid should contain sufficient sulfur trioxide so that it still contains 10 to 50% free sulfur trioxide after the reaction. The resulting products preferably contain an average of 1.3 to 1.8 sulfonic acid groups per aromatic nucleus. Particularly, suitable polymers which contain sulfonic acid groups are copolymers of aromatic monovinyl compounds with aromatic polyvinyl compounds, particularly, divinyl compounds, in which the polyvinyl benzene content is preferably 1 to 20% by weight of the copolymer (see, for example, German Patent Specification No. 908,247).

The ion exchange resin is preferably used in a granular size of about 0.15 to 1 mm, although particles of 250μ up to about 1 mm may be employed. The finer catalysts provide high surface area, but also result in high pressure drops through the reactor.

Quite surprisingly, it has also been found that the present hydration process as described, also converts n-butene-1 to secondary alcohol, which is also a valuable product, and which is easily separated from the ter-butyl alcohol (TBA).

The following examples are illustrative of the invention (or prior art) and are not intended to be determinative of the scope of the invention.

Referring now to the drawing, one mode of operation will be described. The reactor 10 is a vertical stainless steel tubular reactor with the resin catalyst bed 11 supported through the middle portion. The hydrocarbon phase product (the only product phase) is removed via line 12. The stream 12 is split and a portion 13 is sent for storage or processing to recover t-butanol and unreacted isobutene for recycle (not shown) to line 18 which is the isobutene feed. A portion of the hydrocarbon phase product from line 12 passes via 15 for recycle to mix with incoming isobutene feed 18. This stream 15 contains t-butanol, unreacted isobutene and some dimer.

The isobutene feed 18 passes through a heat exchanger 19 where its temperature is adjusted usually by heating and hence, into the recycle line 15. (Note the heating of feed 18 and cooling of recycle 15 may be carried out as the same step by direct or indirect contacting of the two.) Reaction water is added via 20 to the combined streams 18 and 15. The three streams (fresh feed, recycle and water) pass through static mixer 17 into the reactor 10 and down through the resin bed 11. Since there is not an excess of water, only a hydrocarbon phase passes from the bed. The recycle stream is pumped by pump 14 into recycle line 15 which passes through heat exchanger 16 where it is cooled (note above). On startup, the heat exchanger 16 may be used to heat the recycle. Other items of standard equipment are not shown, but would be employed as obviously desirable or necessary, e.g., safety valves, liquid level indicators, drains, vents, etc.

EXAMPLE 1

This example demonstrates a typical prior art process without recycle. The runs were made in a 1 inch ID reactor. The conditions of the process, feed and results are all set forth in Table 1.

TABLE I

Reactor 1" × 24"; Resin 200 mls. (wet); *Amberlyst 15; Temperature 98° – 100° C; Pressure 220 psig; Hydrocarbon, LHSV 1.07; $H_2O$, LHSV 0.42; $H_2O/iC_4$ = Molar Ratio 4.3

| Hours on Stream | | 3.5 | 4.8 | 7.0 | 8.0 |
|---|---|---|---|---|---|
| Gas Analysis**(Mole %) | Feed | | Raffinate | | |
| $iC_4$ | 2.8 | 5.2 | 3.8 | 4.1 | 5.4 |
| $nC_4$ | 6.0 | 8.1 | 8.6 | 8.9 | 8.1 |
| $C_4^=$ | 24.5 | 36.4 | 35.0 | 35.4 | 36.7 |
| $iC_4^=$ | 48.0 | 27.3 | 25.5 | 23.1 | 26.4 |
| Low boiling $C_4^{=2}$ | 10.9 | 13.5 | 16.0 | 16.6 | 13.8 |
| High boiling $C_4^{=2}$ | 4.3 | 4.9 | 6.5 | 7.0 | 5.0 |
| $C_4H_6$ | 3.5 | 4.7 | 4.5 | 5.0 | 4.7 |
| Isobutylene Conversion | | 59.3 | 62.9 | 67.5 | 61.1 |
| Selectivity | | | | | |
| t-BuOH | | 97.6 | 88.9 | 78.3 | 75.9 |
| Dimer | | 2.39 | 11.0 | 20.7 | 23.3 |
| Trimer | | trace | 0.1 | 1.0 | 0.85 |
| Butadiene Conversion | | 5.8 | 10.3 | 4.6 | 6.4 |

*Cation exchange resin, highly crosslinked, macroreticular, sulfonated, 45m² surface area, 32% porosity, 1.8 meq/ml (2,.9 meq/g) exchange capacity. (Rohm and Haas Co.)

**Analytical data for water-TBA is provided by GC using a 4' × 1/8" Porapak QS column at 220° C thermal conductivity detection; for TBA-isobutene dimer, trimer and heavy polymers a 41' × 1/8" DC710 on Teflon column at 220° C with flame ionization detection is used. Appropriate sensitivity factors are used for both columns.

EXAMPLES 2–32

These examples illustrate the invention, and in addition, illustrate a dimerization as discussed above. Comparison of these results, as shown in Table II, with the standard, prior art type of process shown in Example 1, shows very good conversions and selectivities without the water phase, and, in particular, the corrosion problems in regard thereto. Note that a 0.18 : 1 mol ratio water : isobutene (total isobutene) conversion is a remarkable 57.5% and selectivity to TBA is 96.2%. From the prior art, one would not expect such high conversion and high t-butanol selectivity without a substantial excess of water beyond stoichiometric. The reactor was a 12-inch I.D. stainless steel pipe, containing 8.4 cubic feet of Amberlyst 15* resin. The conditions and process variables of each run are specified in Table II.

*Rohm and Haas Company, Phil., PA, Sulfonated polystyrene (divinyl benzene crosslinked); resin beads, (20–50 mesh) having macroreticular structure, cation exchange characterized as strong acid, active group $-SO_3-H+$.

TABLE II

| Example | Fresh Hebn. Feed[1] LHSV | Hebn. Recircn. Rate, gpm | H₂O Injection Rate, lbs/min[6] | Molar Ratio H₂O/iC₄⁼ Based on Feed Only | Molar Ratio H₂O/iC₄⁼ Based on Feed + Recycle | Temp. °F Inlet | Temp. °F Max | iC₄⁼ Conv.[5] Mol % | iC₄⁼ Sel, Mol % TBA | iC₄⁼ Sel, Mol % Dimer and[3] Codimer | iC₄⁼ Sel, Mol % C₉+ | C₄⁼¹ Conv.[5] Mol % | C₄⁼¹ Sel, Mol % trans C₄⁼² | C₄⁼¹ Sel, Mol % cis C₄⁼² | C₄⁼¹ Sel, Mol % Sec-butyl Alcohol | Analysis of Dimer Product[4] Dimer 1 | Analysis of Dimer Product[4] Weight % Dimer 2 | Analysis of Dimer Product[4] Codimer | Analysis of Dimer Product[4] C₉+ |
|---|---|---|---|---|---|---|---|---|---|---|---|---|---|---|---|---|---|---|---|
| 2  | 0.935 | 3.9  | 0.26  | 0.33 | 0.12  | 200 | 221 | 49.3 | 52.9 | 44.4 | 2.72 | —    | —    | —    | —    |      |      |      |      |
| 3  | 1.03  | 3.68 | 0.38  | 0.44 | 0.17  | 204 | 220 | 46.6 | 67.2 | 30.9 | 2.0  | 8.3  | 5.6  | —    | 54.6 |      |      |      |      |
| 4  | 1.03  | 3.68 | 0.38  | 0.44 | 0.17  | 205 | 220 | 45.1 | 71.5 | 27.2 | 1.4  | 8.4  | 20.1 | 11.8 | 39.9 |      |      |      |      |
| 5  | 1.03  | 3.68 | 0.38  | 0.44 | 0.17  | 206 | 220 | 44.5 | 74.5 | 24.4 | 1.05 | 6.0  | 39.3 | 1.45 | 60.7 |      |      |      |      |
| 6  | 0.992 | 3.68 | 0.19  | 0.23 | 0.067 | 217 | 228 | 41.5 | 56.4 | 41.7 | 1.8  | 10.3 | 8.6  | 22.2 | 57.3 |      |      |      |      |
| 7  | 1.05  | 5.03 | 0.22  | 0.24 | 0.070 | 224 | 246 | 45.2 | 46.8 | 51.0 | 2.2  | 18.8 | 1.5  | 24.3 | 41.7 |      |      |      |      |
| 8  | 1.03  | 5.03 | 0.22  | 0.25 | 0.066 | 226 | 240 | 46.4 | 43.5 | 53.8 | 2.7  | 19.8 | 10.3 | 28.5 | 40.1 |      |      |      |      |
| 9  | 1.03  | 5.03 | 0.19  | 0.25 | 0.073 | 228 | 243 | 51.6 | 40.8 | 56.4 | 2.8  | 24.19 |     |      |      |      |      |      |      |
| 10 | 0.99  | 4.3  | 0.25  | 0.30 | 0.065 | 227 | 244 | 54.1 | 33.4 | 62.0 | 4.6  | 23.9 |      |      |      | 66.1 | 23.6 | 6.2  | 3.9  |
| 11 | 0.99  | 4.3  | 0.25  | 0.30 | 0.101 | 221 | 240 | 51.4 | 39.3 | 56.7 | 4.0  | 35.7 |      |      |      | 63.8 | 23.4 | 6.5  | 6.3  |
| 12 | 0.99  | 4.5  | 0.25  | 0.30 | 0.097 | 218 | 239 | 50.0 | 42.4 | 55.1 | 2.5  |      |      |      |      | 64.0 | 23.2 | 7.2  | 5.6  |
| 13 | 0.84  | 4.6  | 0.19  | 0.27 | 0.078 | 217 | 238 | 51.4 | 41.8 | 55.6 | 2.6  |      |      |      |      | 64.4 | 23.8 | 7.2  | 4.5  |
| 14 | 0.84  | 4.6  | 0.19  | 0.27 | 0.077 | 221 | 240 | 51.7 | 41.3 | 55.9 | 2.8  |      |      |      |      | 65.3 | 25.5 | 7.6  | 3.7  |
| 15 | 0.84  | 4.58 | 0.19  | 0.27 | 0.080 | 220 | 243 | 59.4 | 41.5 | 55.3 | 3.2  |      |      |      |      | 62.3 | 23.1 | 7.6  | 4.6  |
| 16 | 0.84  | 4.45 | 0.10  | 0.15 | 0.060 | 224 | 259 | 67.9 | 23.4 | 69.3 | 7.3  |      |      |      |      | 63.7 | 23.3 | 7.9  | 5.3  |
| 17 | 0.81  | 4.52 | 0.10  | 0.18 | 0.060 | 217 | 251 | 63.9 | 24.6 | 68.0 | 7.3  |      |      |      |      | 61.9 | 22.5 | 7.4  | 7.4  |
| 18 | 0.668 | 4.58 | 0.10  | 0.16 | 0.060 | 219 | 249 | 65.6 | 25.0 | 67.2 | 7.8  |      |      |      |      | 61.4 | 22.9 | 7.2  | 8.4  |
| 19 | 0.687 | 4.58 | 0.09  | 0.08 | 0.050 | 224 | 248 | 66.1 | 23.6 | 68.1 | 8.3  |      |      |      |      | 58.0 | 25.9 | 7.9  | 8.3  |
| 20 | 0.865 | 6.7  | 0.06  | 0.08 | 0.036 | 219 | 253 | 74.7 | 13.2 | 73.2 | 14.5 |      |      |      |      | 59.7 | 22.1 | 7.1  | 11.1 |
| 21 | 0.847 | 7.3  | 0.06  | 0.08 | 0.040 | 222 | 248 | 72.7 | 13.4 | 71.9 | 14.7 |      |      |      |      | 60.0 | 21.5 | 7.5  | 11.0 |
| 22 | 0.847 | 7.3  | 0.06  | 0.08 | 0.038 | 219 | 243 | 73.7 | 15.4 | 71.1 | 13.5 |      |      |      |      | 59.9 | 22.7 | 7.9  | 9.5  |
| 23 | 0.82  | 4.8  | 0.31  | 0.45 | 0.12  | 201 | 222 | 49.9 | 77.9 | 21.8 | 0.3  | 12.9 | 2.9  | 31.2 | 19.6 |      |      |      |      |
| 24 | 0.82  | 4.7  | 0.41  | 0.60 | 0.17  | 199 | 215 | 54.7 | 83.2 | 16.5 | 0.1  | 7.4  | 23.2 | 33.9 | 29.0 |      |      |      |      |
| 25 | 0.84  | 4.8  | 0.31  | 0.44 | 0.18  | 209 | 222 | 57.5 | 96.2 | 3.7  | 0.3  | 2.1  | 18.9 | 37.9 | 12.8 |      |      |      |      |
| 26 | 0.84  | 4.8  | 0.31  | 0.44 | 0.17  | 202 | 223 | 56.9 | 95.3 | 4.5  | 0.2  | 2.2  | 20.4 | 34.4 | 33.0 |      |      |      |      |
| 27 | 0.82  | 5.8  | 0.27  | 0.39 | 0.15  | 219 | 229 | 56.4 | 94.3 | 5.5  | 0.2  | 2.8  | 20.5 | 30.9 | 31.1 |      |      |      |      |
| 28 | 0.84  | 5.8  | 0.23  | 0.33 | 0.13  | 219 | 237 | 54.4 | 92.1 | 6.3  | 1.6  | 4.1  | 36.5 | 37.6 | 24.5 |      |      |      |      |
| 29 | 0.60  | 3.42 | 0.31  | 0.61 | 0.19  | 211 | 226 | 54.6 | 93.2 | 6.6  | 0.3  | 2.4  | 26.8 | 36.9 | 25.2 |      |      |      |      |
| 30 | 1.09  | 6.97 | 0.41  | 0.45 | 0.13  | 211 | 224 | 52.4 | 93.1 | 6.5  | 0.4  | 7.6  | 16.7 | 31.7 | 25.4 |      |      |      |      |
| 31 | 0.57  | 7.10 | 0.046 | 0.10 | 0.037 | 215 | 239 | 81.4 | 10.2 | 71.4 | 18.3 | 51.5 | 0.0  | 19.1 | 31.1 | 55.5 | 20.5 | 8.1  | 15.9 |
| 32[2] | 0.84 | 7.3 | 0.13 | 0.16 | .04  | 178 | 201 | 58.8 | 26.3 | 70.7 | 3.1  | 22.4 | 0.0  | 52.0 | 34.4 | 57.7 | 20.3 | 8.0  | 14.2 |

*iC₄⁼ in feed was ~50% (±1.5%) unless specified otherwise. The feed varied over the weeks of the evaluations set out above, the conversions are based on the actual weight % of isobutene (t-butanol) or n-butene (secondary alcohol product) in the feed. A typical feed analysis, e.g., Example 23 is iso-C₄ - 2.79%; n-C₄ - 8.15%; n-C₄⁼¹ - 24.60%; iso-C₄⁼ - 51.19%; trans n-C₄⁼² - 11.12%; cis n-C₄⁼² - 2.16%. The pressure in the reactor was usually ~300 psi (5 or −10), except Example 32 where it was 285 psi. iso-C₄ - 2.65%; n-C₄ - 7.55%; n-C₄⁼¹ - 19.40%; iso-C₄⁼ - 59.97%; trans n-C₄⁼² - 8.49%; cis n-C₄⁼² - 1.94%.
[3] This analysis was carried out, using GC on samples containing TBA.
[4] The dimer analysis was carried out using GC on samples from which TBA had been removed by water washing and is considered more accurate. C₉+ indicates polymers higher than dimer.
[5] Conversion is based on fresh hydrocarbon feed (stream 18) and product (stream 12).
[6] Calculated.

The invention claimed is:

1. A process for the preparation of t-butanol comprising passing water and isobutene in a mol ratio of water::isobutene in the range of 0.06 to 0.24:1 through a fixed bed of acidic cation exchange resin catalyst in liquid phase at a temperature in the range of 65° to 150° C for a sufficient time to react water and isobutene, producing only a hydrocarbon phase, recovering said hydrocarbon phase, containing t-butanol, splitting said hydrocarbon phase, cooling one portion thereof to a temperature in the range of 15° to 110° C and recycling the cooled portion to the reaction.

2. The process according to claim 1 wherein the mol ratio of water:isobutene is less than 0.24:1.

3. The process according to claim 2 wherein the temperature in the fixed bed is in the range of 65° to 120° C.

4. The process according to claim 1 wherein the amount of water is adjusted to provide that no water leaves the catalyst bed.

5. A process for the prepartion of t-butanol comprising:
   a. feeding a stream containing isobutene;
   b. mixing water and said stream in a mol ratio of 0.06 to 0.024:1, water:isobutene;
   c. contacting said mixture of water and isobutene with a granular fixed bed acidic cation exchange resin for a sufficient time to react water and isobutene at a temperature of reaction in the fixed bed in the range of 65° to 150° C.
   d. producing only a hydrocarbon phase product stream containing t-butanol;
   e. splitting the hydrocarbon phase product passing from said fixed bed into two portions;
   f. recovering and removing one portion of said hydrocarbon phase product;
   g. cooling one portion said hydrocarbon phase product to a temperature in the range of 15° to 110° C; and,
   h. recycling said cooled hydrocarbon phase product portion to step (a) or (b).

6. The process according to claim 5 wherein the temperature in the reaction in the fixed bed is in the range of 90° to 120° C.

7. The process according to claim 6 wherein the temperature gradient in the fixed bed is no greater than 25° C.

8. The process according to claim 5 wherein the mol ratio of water to isobutene is less than 0.2:1.

9. The process according to claim 5 wherein the acidic cation exchange resin contains sulfonic acid groups.

10. The process according to claim 5 wherein the resin has a granular size of about 0.15 to 1 mm.

11. The process according to claim 5 wherein said cooled hydrocarbon phase product portion is continuously recycled to step (a).

12. The process according to claim 5 wherein said isobutene is a component of a stream substantially comprising $C_4$ hydrocarbons.

13. The process according to claim 12 wherein said isobutene comprises 5 to 100 percent of said $C_4$ hydrocarbons.

14. The process according to claim 5 wherein said mixture of water and isobutene flow concurrently downward through said fixed bed.

15. The process according to claim 5 wherein said fixed bed is positioned in a vertical reactor.

16. The process according to claim 5 wherein the recycle hydrocarbon phase of step 5 (h) is returned to step 5 (a) or (b), in a volume ratio of 1 to 50:1, recycle:isobutene of step (a).

17. The process according to claim 5 wherein t-butanol is recovered from the hydrocarbon phase product of step (f).

18. The process according to claim 5 wherein all of the water contacting said fixed bed acidic cation exchange resin is consumed in the reaction.

* * * * *